US00PP34643P3

(12) United States Plant Patent
Post

(10) Patent No.: US PP34,643 P3
(45) Date of Patent: Oct. 11, 2022

(54) ***CHRYSANTHEMUM* PLANT NAMED 'DLFMEXI4'**

(50) Latin Name: ***Chrysanthemum* X *morifolium***
Varietal Denomination: DLFMEXI4

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/548,557

(22) Filed: Dec. 12, 2021

(65) Prior Publication Data

US 2022/0192067 P1 Jun. 16, 2022

Related U.S. Application Data

(60) Provisional application No. 63/124,834, filed on Dec. 13, 2020.

(51) Int. Cl.
*A01H 5/02* (2018.01)
*A01H 6/14* (2018.01)

(52) U.S. Cl.
USPC ..... Plt./298
CPC ..... *A01H 6/1424* (2018.05); *A01H 5/02* (2013.01)

(58) Field of Classification Search
USPC ..... Plt./286, 298
See application file for complete search history.

(56) References Cited

PUBLICATIONS

CPVO Register Application Consultation S2/S3 Publication, version 4.1.51; citation for'DLFMEXI4' (Retrieved form the Internet on May 5, 2022) (3 pages total).*

* cited by examiner

*Primary Examiner* — Susan McCormick Ewoldt
(74) *Attorney, Agent, or Firm* — C. Anne Whealy

(57) ABSTRACT

A new and distinct cultivar of *Chrysanthemum* plant named 'DLFMEXI4', characterized by its upright plant habit; uniform growth habit; uniform and freely flowering habit; dark green-colored leaves; strong upright flowering stems; single-type inflorescences with deep red-colored ray florets and yellowish green-colored disc florets; resistance to Fusarium, White Rust and Western Flower Thrips; relative tolerance to high and low production temperatures; and good postproduction longevity.

1 Drawing Sheet

Figure 1:
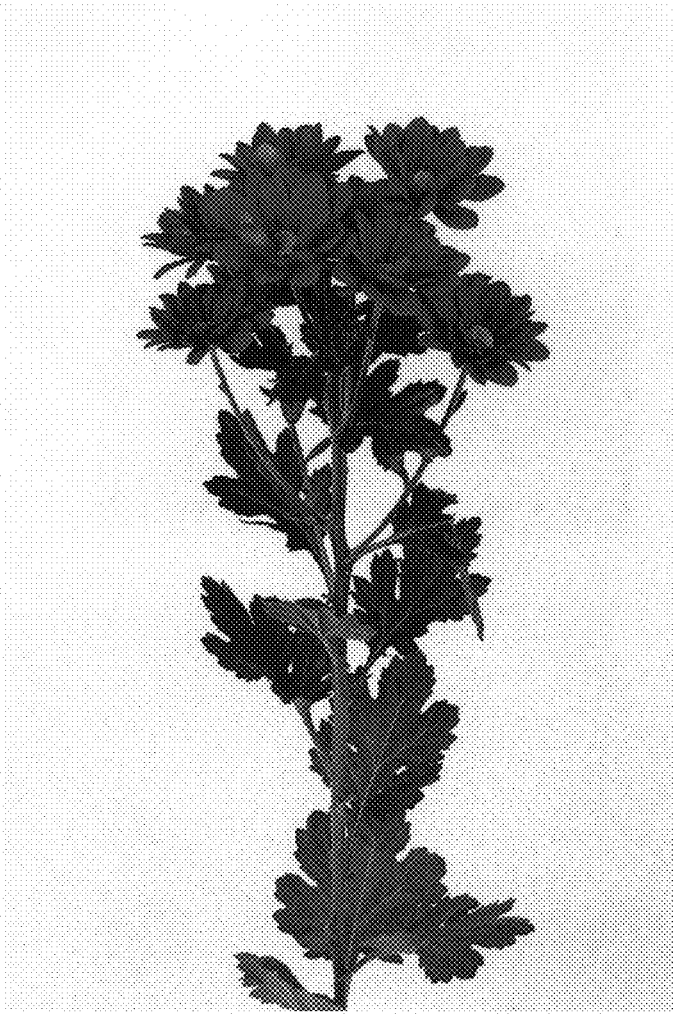

Botanical designation: *Chrysanthemum* X *morifolium*.
Cultivar denomination: 'DLFMEXI4'.

CROSS-REFERENCED TO CLOSELY-RELATED APPLICATIONS

Title: Varieties of *Chrysanthemum* Plants
Inventor/Applicant: Arie Gerard Post
Filed: Dec. 13, 2020
Ser. No.: 63/124,834
Inventor/Applicant hereby claims the priority benefit of this provisional U.S. Patent Application.

STATEMENT REGARDING PRIOR DISCLOSURES BY INVENTOR/APPLICANT & ASSIGNEE

An European Plant Breeder's Rights application for the instant plant was filed by the Assignee, Deliflor Royalties B.V. of Maasdijk, The Netherlands on Feb. 16, 2021, application number 2021/0505. Foreign priority is not claimed to this application.

A Japanese Plant Breeder's Rights application for the instant plant was filed by the Assignee, Deliflor Royalties B.V. of Maasdijk, The Netherlands on Sep. 8, 2021, application number 35706. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFMEXI4'.

The new *Chrysanthemum* plant is a product of a planned breeding program conducted by the Inventor in Maasdijk, The Netherlands. The objective of the breeding program is to create new cut flower *Chrysanthemum* plants with unique and attractive inflorescences.

The new *Chrysanthemum* plant originated from a cross-pollination in September, 2017 of a proprietary selection of *Chrysanthemum* x *morifolium* identified as code number db 58286, not patented, as the female, or seed, parent with a proprietary selection of *Chrysanthemum* x *morifolium* identified as code number db 56123, not patented, as the male, or pollen, parent. The new *Chrysanthemum* plant was discovered and selected as a single flowering plant from within the progeny of the stated cross-pollination in a controlled greenhouse environment in Maasdijk, The Netherlands in September, 2018.

Asexual reproduction of the new *Chrysanthemum* plant by vegetative terminal cuttings since September, 2018 in a controlled greenhouse environment in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFMEXI4'. These characteristics in combination distinguish 'DLFMEXI4' as a new and distinct *Chrysanthemum* plant:

1. Upright plant habit; uniform growth habit.
2. Uniform and freely flowering habit.
3. Dark green-colored leaves.
4. Strong upright flowering stems.
5. Single-type inflorescences with deep red-colored ray florets and greenish yellow-colored disc florets.
6. Resistant to Fusarium (*Fusarium oxysporum*), White Rust (*Puccinia horiana*) and Western Flower Thrips.
7. Relatively tolerant to high and low production temperatures.
8. Good postproduction longevity.

Plants of the new *Chrysanthemum* differ primarily from plants of the female parent selection in leaf shape as leaves of plants of the new *Chrysanthemum* are shorter and broader than leaves of plants of the female parent selection are purplish pink in color. In addition, ray florets of plants of the new *Chrysanthemum* have bluntly acute to shallowly praemorse apices whereas ray florets of plants of the female parent selection have emarginate apices.

Plants of the new *Chrysanthemum* differ primarily from plants of the male parent selection in disc floret color as disc florets of plants of the new *Chrysanthemum* are greenish yellow in color whereas disc florets of plants of the male parent selection are more yellow in color.

Plants of the new *Chrysanthemum* can be compared to plants of *Chrysanthemum* X *morifolium* 'DLFHAI4', not patented. In side-by-side comparisons, plants of the new *Chrysanthemum* differ primarily from plants of 'DLFHAI4' in ray floret color as ray florets of plants of the new *Chrysanthemum* are darker red than ray florets of plants of 'DLFHAI4'. In addition, ray florets of plants of the new *Chrysanthemum* are straighter and not as reflexing as ray florets of plants of 'DLFHAI4.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph at the top of the sheet (FIG. 1) comprises a side perspective view of a typical flowering stem of 'DLFMEXI4' grown as a spray-type cut flower.

Figure 2:
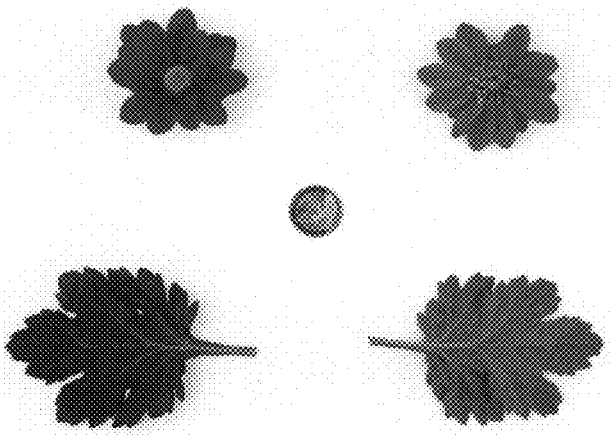

The photograph at the bottom of the sheet (FIG. 2) is a close-up view of upper (left) and lower (right) surfaces of typical inflorescences and typical leaves of 'DLFMEXI4'.

DETAILED BOTANICAL DESCRIPTION

The aforementioned photographs and following observations and measurements describe plants grown during the late winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 7 klux. Plants were grown as single-stem spray-type plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFMEXI4'.

Parentage:

*Female, or seed, parent.*—Proprietary selection of *Chrysanthemum* x *morifolium* identified as code number db 58286, not patented.

*Male, or pollen, parent.*—Proprietary selection of *Chrysanthemum* x *morifolium* identified as code number db 56123, not patented.

Propagation:

*Type.*—Terminal vegetative cuttings.

*Time to initiate roots, summer.*—About four days at temperatures about 20° C.

*Time to initiate roots, winter.*—About six days at temperatures about 20° C.

*Time to produce a rooted young plant, summer.*—About 13 days at temperatures about 20° C.

*Time to produce a rooted young plant, winter.*—About 15 days at temperatures about 20° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous single-type cut flower that is typically grown as a single stem spray-type; upright plant habit; vigorous growth habit and rapid growth rate.

*Plant height, soil level to top of foliar plane.*—About 70.9 cm.

*Plant height, soil level to top of inflorescence plane.*—About 77.8 cm.

*Plant (spray) diameter.*—About 16.6 cm.

*Flowering stem length.*—About 67.7 cm.

*Flowering stem diameter.*—About 7 mm.

*Flowering stem internode length.*—About 2.9 cm.

*Flowering stem strength.*—Strong.

*Flowering stem aspect.*—Erect.

*Flowering stem texture and luster*.—Densely pubescent; slightly glossy.

*Flowering stem color, developing*.—Close to 144A.

*Flowering stem color, developed*.—Close to 146A; at the ridges, tinged with close to 197A.

*Leaf description*.—Arrangement: Alternate; simple. Length: About 11.2 cm. Width: About 7.7 cm. Shape, in overall outline: Broadly oblong. Apex: Abruptly acute, minute. Base: Attenuate. Margin: Palmately lobed, coarsely dentate to serrate; sinuses convergent and medium to deep in depth; slightly undulate. Texture and luster, upper surface: Moderately pubescent, not rugose; slightly velvety; slightly glossy. Texture and luster, lower surface: Moderately pubescent, prominent venation; slightly glossy. Venation pattern: Pinnate, reticulate. Color: Developing leaves, upper surface: Close to NN137B. Developing leaves, lower surface: Close to 147B. Fully developed leaves, upper surface: Close to NN137A; venation, close to 146A. Fully developed leaves, lower surface: Close to between 146A and 147B; venation, close to 146B. Petioles: Length: About 1.4 cm. Diameter: About 3 mm by 5 mm. Strength: Moderately strong. Texture and luster, upper and lower surfaces: Densely pubescent; slightly glossy. Color, upper surface: Close to 147C; edges, close to 146A. Color, lower surface: Close to 146C; edges, close to 146A. Stipules: Quantity and appearance: Two leafy stipules, opposite, at the petiole attachment to the stem. Length: About 5 mm. Width: About 3 mm. Shape, in overall outline: Broadly ovate; apex, acute to occasionally deeply incised; base, broadly cuneate. Texture and luster, upper and lower surfaces: Moderately pubescent; slightly glossy. Color, upper surface: Close to NN137A. Color, lower surface: Close to between 146A and 147B.

Inflorescence description:

*Appearance*.—Single-type inflorescence form with obovate to broadly elliptic-shaped ray florets and tubular disc florets; inflorescences borne perpendicular to peduncles and face upright to slightly outwardly; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 54 days later when grown as a spray-type.

*Postproduction longevity*.—Good postproduction longevity; after a seven-day storage period, cut flowers will maintain good color and substance for about two weeks in an interior environment; inflorescences persistent.

*Quantity of inflorescences*.—Only grown as a spray-type, about 14 inflorescences develop per flowering stem.

*Inflorescence size*.—Diameter, grown as a spray-type: About 7.4 cm. Depth (height), grown as a spray-type: About 2.9 cm. Disc diameter: About 1.7 cm.

*Receptacles*.—Height: About 4 mm. Diameter: About 6 mm. Shape: Flattened globular. Color: Close to 145D.

*Inflorescence buds*.—Height: About 9 mm. Diameter: About 1.2 cm. Shape: Flattened spherical. Texture and luster: Moderately; slightly glossy. Color: Developing involucral bracts, close to 143A and 145C; developing ray florets, close to N77B.

*Ray florets*.—Quantity and arrangement: About 32 arranged in about three whorls. Length: About 3.4 cm, varying between 3 cm and 3.9 cm. Width: About 1.5 cm, varying between 1.3 cm and 1.6 cm. Shape: Obovate to broadly elliptic; moderately concave and moderately carinate. Apex: Bluntly acute to shallowly praemorse. Base: Cuneate. Margin: Entire; not undulate. Aspect: About 60° from vertical. Texture and luster, upper surface: Smooth, glabrous; moderately velvety; matte. Texture and luster, lower surface: Smooth, glabrous; slightly velvety; slightly glossy. Color: When opening, upper surface: Close to 59A and 187C. When opening, lower surface: Close to 184B. Fully opened, upper surface: Close to between 53A and 60A; venation, close to 53A and 60A; color does not change with subsequent development. Fully opened, lower surface: Close to 184B and 184C; venation, close to 185B; color does not change with subsequent development.

*Disc florets*.—Quantity and arrangement: About 160 spirally arranged in about seven whorls at the center of the receptacle. Length: About 6.5 mm. Diameter: About 2 mm. Shape: Tubular; proximally, 85% fused and distally, 15% free. Apex: Acute. Margin, free-part: Entire. Texture and luster, inner and outer surfaces: Smooth, glabrous; glossy. Color: When developing, inner and outer surfaces: Distally, close to N144A and proximally, close to 145D. Fully developed, inner and outer surfaces: Distally, close to 6B and proximally, close to 145D.

*Involucral bracts*.—Quantity and arrangement: About 28 arranged in about three whorls. Length: About 9 mm. Width: About 3 mm. Shape: Oblong. Apex: Obtuse. Base: Cuneate. Margin: Entire. Texture and luster, upper surface: Smooth, glabrous; glossy. Texture and luster, lower surface: Sparsely pubescent; matte. Color, upper surface: Close to 136B; lateral margins, translucent and close to 145D and 157A and apical margins tinged with close to N199A. Color, lower surface: Close to NN137B; lateral margins, translucent and close to 145D and 157A and apical margins tinged with close to N199A.

*Peduncles*.—Length, terminal peduncle: About 4.3 cm. Diameter, terminal peduncle: About 3 mm. Length, third peduncle, grown as a spray-type: About 8 cm. Diameter, third peduncle, grown as a spray-type: About 2.75 mm. Strength: Strong. Aspect, terminal peduncle: Upright. Aspect, third peduncle: About 40° from the flowering stem axis. Texture and luster: Moderately pubescent; moderately glossy. Color: Close to 143A.

*Reproductive organs*.—Androecium: Present on disc florets only. Quantity: About five per floret. Filament length: About 3 mm. Filament color: Close to 151D.

Anther size: About 0.5 mm by 2 mm. Anther shape: Oblong. Anther color: Close to 153D. Pollen amount: Scarce. Pollen color: Close to 12A. Gynoecium: Present on both ray and disc florets. Quantity: One per floret. Pistil length: About 6 mm. Style length: About 5 mm. Style color: Close to 145C. Stigma diameter: About 1 mm. Stigma shape: Cleft, decurrent. Stigma color: Close to 153D. Ovary color: Close to 157A.

*Seeds and fruits*.—To date, seed and fruit development have not been observed on plants of the new *Chrysanthemum.*

Pathogen & pest resistance: Plants of the new *Chrysanthemum* have been observed to be resistant to Fusarium (*Fusarium oxysporum*), White Rust (*Puccinia horiana*) and Western Flower Thrips. To date, plants of the new *Chrysanthemum* have not been observed to be resistant to other pathogens and pests common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFMEXI4' as illustrated and described.

* * * * *